United States Patent
Cheung et al.

(10) Patent No.: US 9,916,424 B2
(45) Date of Patent: Mar. 13, 2018

(54) EARLY EXACERBATION DETECTION USING DIFFERENTIAL TEMPERATURE MONITORING

(75) Inventors: Amy Oi Mee Cheung, Eindhoven (NL); Jasper Klewer, Eindhoven (NL); Maryam Atakhorrami, Cambridge (GB)

(73) Assignee: Koninklijke Philips N.V., Eindhoven (NL)

( * ) Notice: Subject to any disclaimer, the term of this patent is extended or adjusted under 35 U.S.C. 154(b) by 751 days.

(21) Appl. No.: 13/518,066

(22) PCT Filed: Nov. 17, 2010

(86) PCT No.: PCT/IB2010/055225
§ 371 (c)(1),
(2), (4) Date: Jun. 21, 2012

(87) PCT Pub. No.: WO2011/080602
PCT Pub. Date: Jul. 7, 2011

(65) Prior Publication Data
US 2012/0302911 A1    Nov. 29, 2012

Related U.S. Application Data

(60) Provisional application No. 61/290,347, filed on Dec. 28, 2009.

(51) Int. Cl.
*A61B 5/00* (2006.01)
*G06F 19/00* (2018.01)

(52) U.S. Cl.
CPC ........ *G06F 19/345* (2013.01); *G06F 19/3487* (2013.01)

(58) Field of Classification Search
CPC ........ A61B 5/01; A61B 5/015; G01K 13/002
USPC ................................ 600/473, 474, 475, 549
See application file for complete search history.

(56) References Cited

U.S. PATENT DOCUMENTS

| 3,933,045 | A | 1/1976 | Fox | |
|---|---|---|---|---|
| 4,453,552 | A * | 6/1984 | Ensign | 600/549 |
| 7,299,090 | B2 | 11/2007 | Koch | |
| 2003/0092975 | A1 * | 5/2003 | Casscells et al. | 600/300 |
| 2007/0265542 | A1 | 11/2007 | Bardy | |
| 2011/0069459 | A1 | 3/2011 | Padiy | |
| 2011/0317737 | A1 | 12/2011 | Klewer | |

FOREIGN PATENT DOCUMENTS

| WO | WO2004026131 A1 | 4/2004 |
|---|---|---|
| WO | WO2005096920 A1 | 10/2005 |
| WO | WO2007052108 A2 | 5/2007 |
| WO | WO2008068665 A1 | 6/2008 |
| WO | WO2008078271 A1 | 7/2008 |

(Continued)

*Primary Examiner* — Daniel Cerioni
(74) *Attorney, Agent, or Firm* — Michael W. Haas

(57) ABSTRACT

A system and method for predicting an onset of an exacerbation in a patient is provided. The method includes monitoring core body temperature of the patient; monitoring breath temperature of the patient; calculating a relationship, or a change in relationship, between the core body temperature and the breath temperature of the patient; and detecting the onset of the exacerbation, when the calculated relationship, or a change in relationship, satisfies a predetermined criteria.

17 Claims, 6 Drawing Sheets

(56) References Cited

FOREIGN PATENT DOCUMENTS

| WO | WO2008110947 A1 | 9/2008 |
| WO | WO2008110948 A2 | 9/2008 |
| WO | WO2008110949 A1 | 9/2008 |
| WO | WO2009107009 A2 | 9/2009 |
| WO | WO2009138896 A1 | 11/2009 |
| WO | WO2010082102 A2 | 7/2010 |
| WO | WO2010103436 A1 | 9/2010 |
| WO | WO2010116297 A1 | 10/2010 |

* cited by examiner

Exhaled breath temperature increase ($\Delta e° T$) in normal subjects and patients with chronic obstructive pulmonary disease (COPD). *: $p<0.05$; **: $p<0.01$.

EARLY EXACERBATION DETECTION USING DIFFERENTIAL TEMPERATURE MONITORING

CROSS-REFERENCE TO RELATED APPLICATIONS

This patent application claims the priority benefit under 35 U.S.C. § 371 of international patent application no. PCT/IB2010/055225, filed Nov. 17, 2010, which claims the priority benefit under 35 U.S.C. § 119(e) of U.S. Provisional Application No. 61/290,347 filed on Dec. 28, 2009, the contents of which are herein incorporated by reference.

BACKGROUND OF THE INVENTION

1. Field of the Disclosure

The present invention relates to a system and a method for predicting an onset of an exacerbation in a patient.

2. Description of the Related Art

Chronic Obstructive Pulmonary Disease (COPD) is a respiratory disease that is characterized by inflammation of the airways. It is characterized by an airflow limitation that is not fully reversible. The airflow limitation is both progressive and associated with an abnormal inflammatory response of the lungs to noxious particles or gases. Symptoms of COPD may include coughing, wheezing and the production of mucus and the degree of severity can, in part, be viewed in terms of the volume and color of secretions.

Exacerbations are the worsening of COPD symptoms. The exacerbations may be associated with a variable degree of physiological deterioration. The exacerbations may be characterized by increased coughing, dyspnea (i.e., shortness of breath) and production of sputum. Typically, exacerbations are detected by a general practitioner or a hospital physician. In clinical trials, questionnaires are used to identify the occurrence of an exacerbation.

The exacerbations are normally caused by viral or bacterial infections and depending on the severity may lead to hospitalization of the COPD patients. The frequency of exacerbations increases during the winter months due to cold stresses on the patient's body. This may be due to a combination of a) the cooling of facial skin and airways, resulting in bronchoconstriction, and b) the thermoregulatory system becoming less effective with age, thus making COPD patients more susceptible for respiratory infections.

The exacerbations not only limit the performance of daily activities, but also significantly decrease the health related quality of life of COPD patients. A high frequency of exacerbations is linked to a poor prognosis for survival. Also, the exacerbations often may result in hospitalization, which is the main determinant of the overall healthcare expenditure for COPD patients.

Because of the damage done when an exacerbation takes place, it is desirable to predict the likely onset of an exacerbation and initiate treatments, which either prevents the exacerbation from occurring and/or treats the symptoms at an early stage, thereby reducing the damage caused by the exacerbation. Moreover, reducing and most importantly preventing exacerbations may help COPD patients lead an improved quality of life and may lower the healthcare costs for COPD patients.

SUMMARY OF THE INVENTION

One aspect of the present invention provides a method for predicting an onset of an exacerbation in a patient. The method includes monitoring core body temperature of the patient; monitoring breath temperature of the patient; calculating a relationship, or a change in relationship, between the core body temperature and the breath temperature of the patient; and detecting the onset of the exacerbation, when the calculated relationship, or a change in relationship, satisfies a predetermined criteria.

Another aspect of the present invention provides a system for predicting an onset of an exacerbation in a patient. The system includes a temperature sensor, a breath temperature sensor, and a processor. The temperature sensor is configured to monitor core body temperature of the patient. The breath temperature sensor is configured to monitor breath temperature of the patient. The processor is configured a) to calculate a relationship, or a change in relationship, between the core body temperature and the breath temperature of the patient, and b) to detect the onset of the exacerbation, when the calculated relationship, or a change in relationship, satisfies a predetermined criteria.

Another aspect of the present invention provides a method for predicting an onset of an exacerbation in a patient. The method includes monitoring skin temperature of the patient; and detecting the onset of the exacerbation, when the monitored skin temperature of the patient is less than a predetermined threshold, or a drop in the monitored skin temperature of the patient exceeds a predetermined temperature drop, coupled with the core body temperature and/or the breath temperature a) increasing by a predetermined amount, b) remaining constant, or c) dropping by an amount less than the drop in skin temperature either on an absolute or percentage basis.

Another aspect of the present invention provides a system for predicting an onset of an exacerbation in a patient. The system includes a skin temperature sensor, and a processor. The skin temperature sensor is configured to monitor skin temperature of the patient. The processor is configured to detect the onset of the exacerbation, when the monitored skin temperature of the patient is less than a predetermined threshold, or a drop in the monitored skin temperature of the patient exceeds a predetermined temperature drop; and coupled with the core body temperature and/or the breath temperature a) increasing by a predetermined amount, b) remaining constant, or c) dropping by an amount less than the drop in skin temperature either on an absolute or percentage basis.

These and other aspects of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. It shall also be appreciated that the features of one embodiment disclosed herein can be used in other embodiments disclosed herein.

DETAILED DESCRIPTION OF EXEMPLARY EMBODIMENTS

Figure 1A:
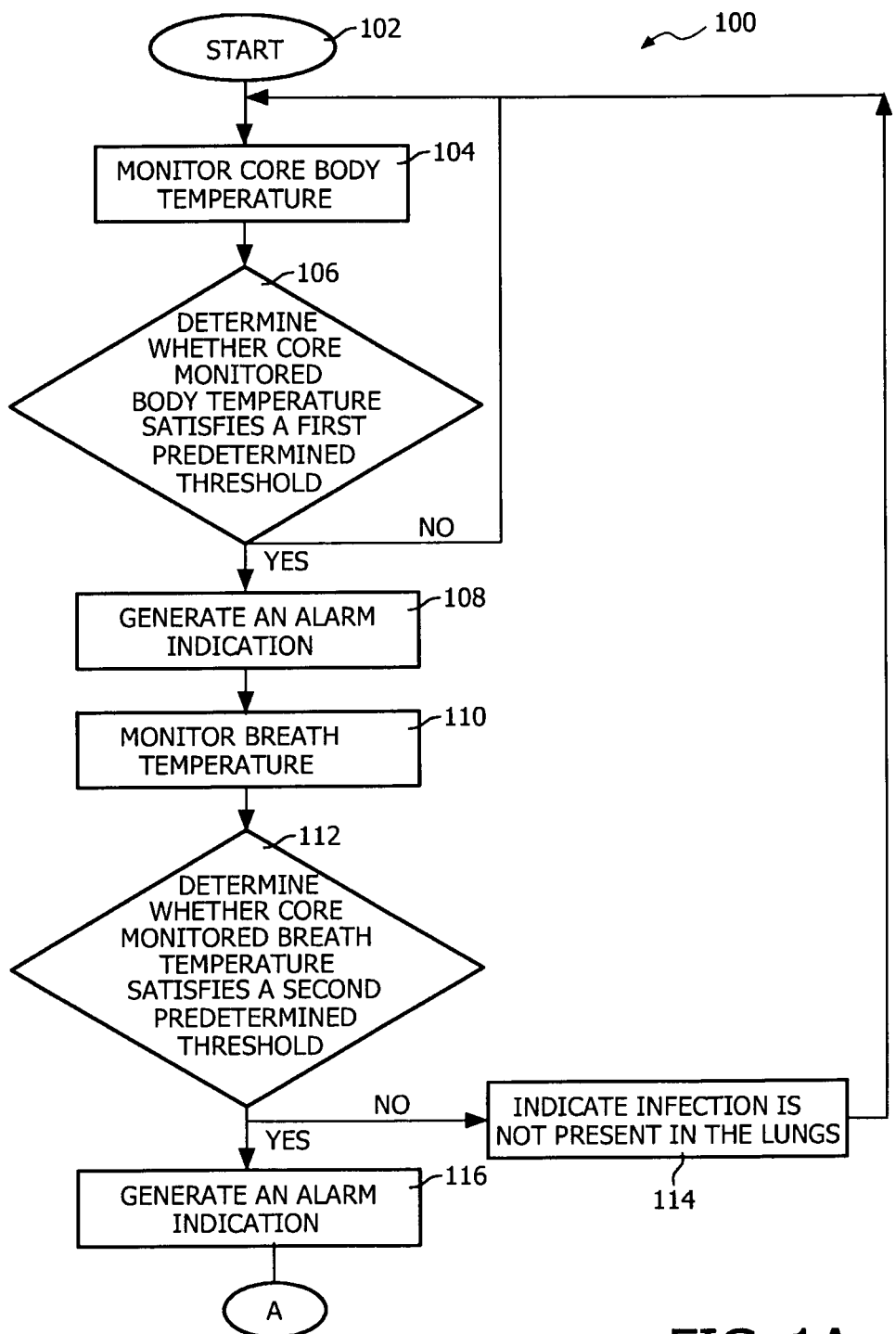
FIGS. 1A and 1B illustrate a flow chart for a method for predicting an onset of an exacerbation in a patient in accordance with an embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 1B:
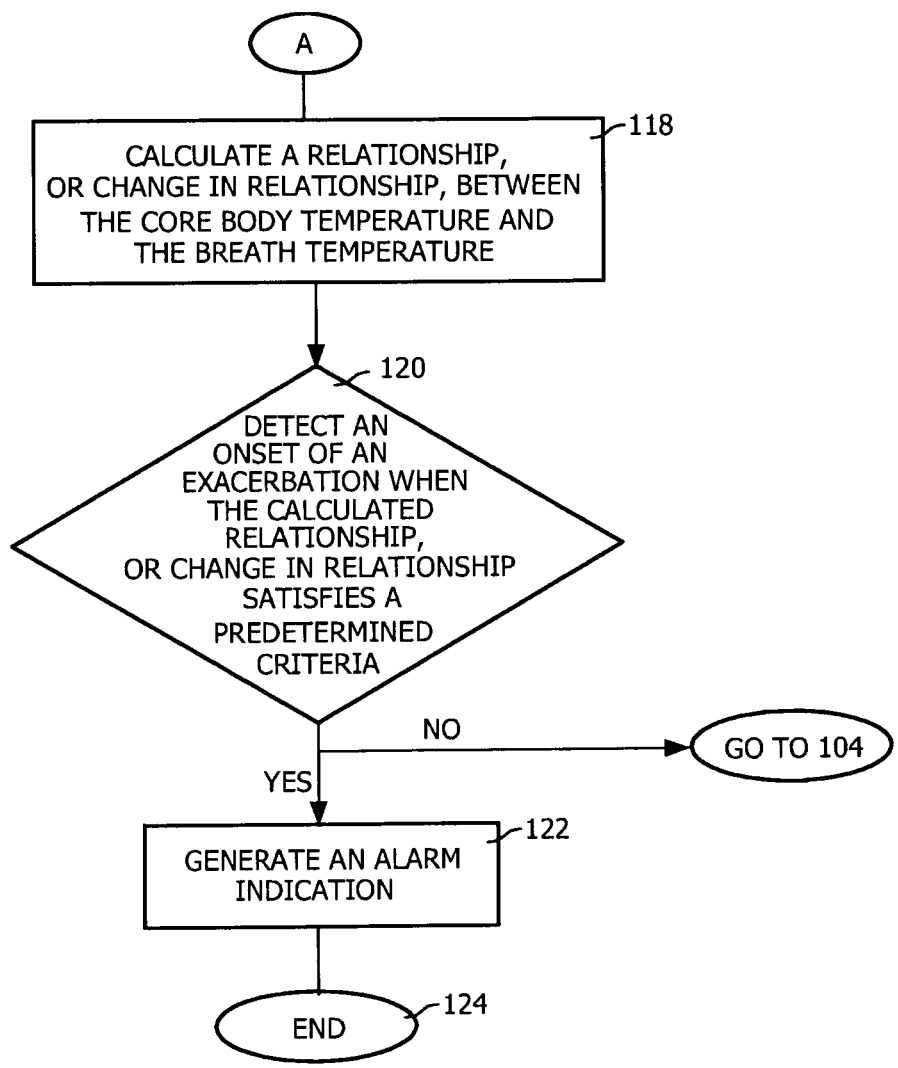

FIGS. 1A and 1B illustrate a flow chart for a method 100 for predicting an onset of an exacerbation in a patient suffering from COPD in accordance with an embodiment of the present invention. Method 100 is configured to detect early exacerbation using a relationship, or a change in relationship, between core body temperature of the patient and (exhaled) breath temperature of the patient. In one embodiment, a change in relationship in the breath temperature may be used in addition to using the relationship, or a change in relationship, between core body temperature of the patient and (exhaled) breath temperature of the patient.

The body's natural defense mechanism to an infection is an elevation in the core body temperature. Therefore, monitoring of the core body temperature of the patient may provide an indication of an infection in the patient. A warning signal is subsequently provided to the patient to conduct a breath temperature measurement to ascertain if the infection is present in the lungs (and hence may lead to an exacerbation) or an infection elsewhere in the body. The relationship, or a change in relationship, between the core body temperature and the exhaled breath temperature may also provide further information, for example, related to inflammation of the lungs.

Method 100 begins at procedure 102. At procedure 104, a core body temperature of the patient is monitored. The core body temperature of the patient is monitored using a temperature sensor, such as sensor 302 (as shown in and explained with respect to FIG. 3).

At procedure 106, a processor 310 (as shown in and explained with respect to FIG. 3) is configured to determine whether the monitored core body temperature satisfies a first predetermined threshold. In one embodiment, the first predetermined criteria is a core body temperature greater than a temperature of 37° C. In another embodiment, the first predetermined criteria can be a temperature threshold greater than 37° C. (e.g., 39° C., 40° C., or 41° C., just for example).

If the monitored core body temperature satisfies the first predetermined threshold, then method 100 proceeds to procedure 108. Otherwise, method 100 returns to procedure 104 where the core body temperature of the patient is monitored.

Figure 3:
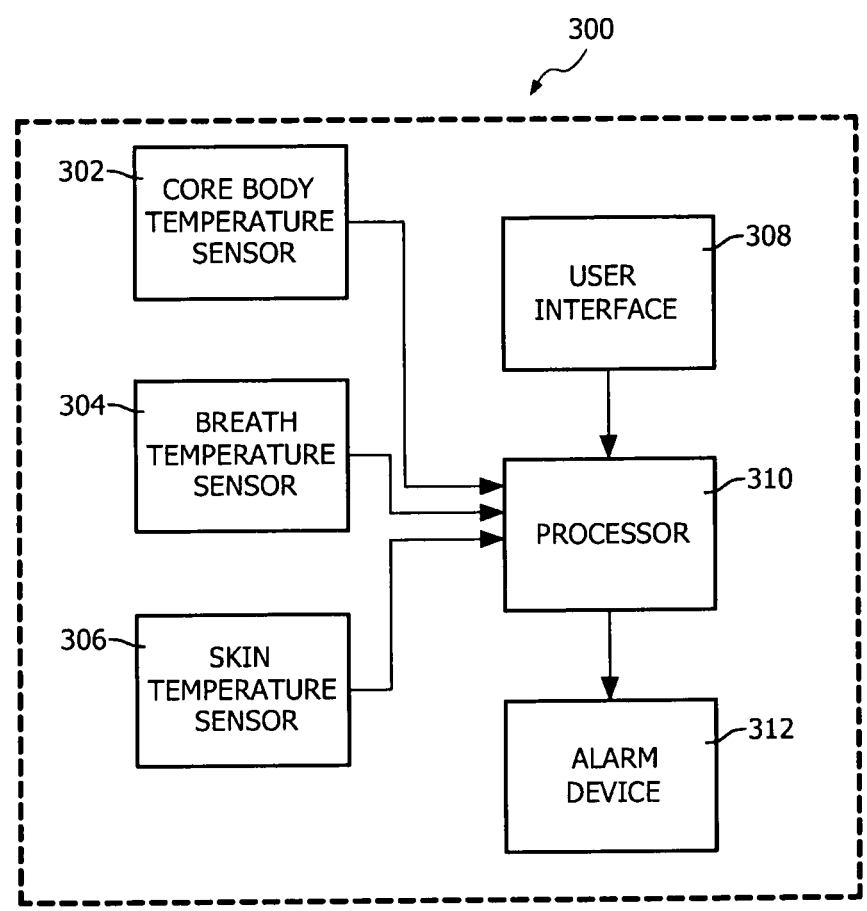
FIG. 3 is a system for predicting the onset of an exacerbation and/or the onset of cold stresses in the patient in accordance with an embodiment of the present invention.

At procedure 108, an alarm indication or a warning may be generated by an alarm device, such as an alarm device 312 (as shown in and explained with respect to FIG. 3). The alarm indication may be generated to indicate that an infection is detected in patient's body. The alarm indication may also be generated to alert the patient to assess their breath temperature to determine (or ascertain) if the infection is present in the patient's lungs (as will be explained below).

At procedure 110, the breath temperature of the patient is monitored. The breath temperature of the patient is monitored using a breath temperature sensor, such as sensor 304 (as shown in and explained with respect to FIG. 3).

In one embodiment, when the core body temperature of the patient satisfies the first predetermined threshold, the warning signal or the alarm indication is trigged (by alarm device 312 at procedure 108) to alert the patient to assess their breath temperature to determine (or ascertain) if the infection is present in the patient's lungs. In another embodiment, the breath temperature of the patient may be automatically monitored by processor 310, when the core body temperature of the patient satisfies the first predetermined threshold.

At procedure 112, processor 310 (as shown in and explained with respect to FIG. 3) is configured to determine whether the monitored breath temperature satisfies a second predetermined threshold. In one embodiment, the second predetermined criteria is a breath temperature greater than a temperature of 35° C. In another embodiment, the second predetermined criteria can be a temperature threshold greater than 35° C. (e.g., 37° C., 38° C., 38° C. or 40° C., just for example).

If the monitored breath temperature satisfies the second predetermined threshold, then method 100 proceeds to procedure 116. Otherwise, the method proceeds to procedure 114 where an indication or a signal is provided to the patient that the infection is not present in the patient's lungs. In other words, the infection may be present elsewhere in the body and not in the patient's lungs. Method 100 from procedure 114 returns to procedure 104 to monitor of the core body temperature of the patient.

At procedure 116, an alarm indication or a warning may be generated by alarm device 312 (as shown in and explained with respect to FIG. 3). The alarm indication can optionally be different than that of procedure 108, and may be generated to indicate that an infection is detected in patient's lungs.

At procedure 118, processor 310 (as shown in and explained with respect to FIG. 3) is configured to calculate a relationship, or a change in relationship, between the core body temperature of the patient and the breath temperature of the patient.

At procedure 120, processor 310 (as shown in and explained with respect to FIG. 3) is configured to detect an onset of an exacerbation, when the determined relationship, or change in relationship, satisfies a predetermined criteria. If the calculated relationship, or change in relationship, satisfies the predetermined criteria, method 100 proceeds to procedure 122. Otherwise, the method proceeds to procedure 104 where the core body temperature of the patient is monitored.

In one embodiment, processor 310 is configured to detect an onset of an exacerbation when the breath temperature increased by a certain amount either in absolute terms or in percentage terms, relative to the core body temperature. In another embodiment, the processor is configured to detect an onset of an exacerbation, when an absolute temperature difference between the core body temperature and the breath temperature has decreased by a certain amount. In other words, processor 310 is configured to detect an onset of an exacerbation, when the delta between the breath temperature and the body temperature becomes less. This delta can be measured in absolute terms or in percentage terms.

The breath temperature of a healthy person is generally around 35° C. and the core body temperature of a healthy person is generally around 37° C., and therefore the absolute difference between the core body temperature and the breath temperature for a healthy person is generally around 2° C. In one embodiment, processor 310 is configured to detect an onset of an exacerbation, when the absolute difference between the core body temperature and the breath temperature has decreased by a certain amount (e.g., 0.5° C., 1° C. or 1.5° C.) from 2° C. (i.e., the absolute difference between the core body temperature and the breath temperature for a healthy person). That is, processor 310 is configured to detect an onset of an exacerbation, when the absolute difference between the core body temperature and the breath temperature is, for example, 0.5° C., 1° C. or 1.5° C.

In another embodiment, processor 310 is configured to detect an onset of an exacerbation, when the relative percentage change of breath temperature is greater than the relative percentage change of the core body temperature. For example, if both the core body temperature and the breath temperature increase by 1° C., the relative percentage increase will be greater for the breath temperature. It can thus be appreciated that even if the core body temperature increases by slightly more than the breath temperature, the percentage change of the breath temperature may be slightly greater than the percentage change of the core body temperature.

It should be appreciated that an increase in core body temperature is used in accordance with this disclosure to detect a possible infection or other problem, and if that is detected, then a predetermined increase in the breath temperature can be used to determined that the infection or problem may be coming from the lungs.

Processing device 310 is configured to calculate a relative percentage change of the core body temperature from when the patient is healthy (i.e., when the core body temperature of the patient is 37° C.). In one embodiment, the relative percentage change of the core body temperature is calculated by a) determining an absolute difference between a current value of the core body temperature and the temperature of 37° C.; b) dividing this difference by the temperature of 37° C.; c) multiplying the result (i.e., obtained by dividing the difference by 37° C.) by 100 to obtain the relative percentage change of the core body temperature. The current value of the core body temperature is obtained from core body temperature sensor 302.

In the embodiment discussed above, the core body temperature of the healthy person is taken as 37° C. However, it is contemplated that in another embodiment, the core body temperature of the healthy person may be any temperature between 36.8° C. and 37.4° C. In one embodiment, the core body temperature of the healthy person may be optionally chosen based on patient's history. It is also contemplated that in yet another embodiment, the ambient temperature may be used as the temperature to compare the difference between the current value of the core body temperature and the core body temperature when the person is healthy (e.g., 37° C.) to, for example, divide the difference by the ambient temperature (i.e., instead of 37° C.). In one embodiment, the temperature may be measured in Kelvin or Fahrenheit units.

Processing device 310 is configured to calculate a relative percentage change of the breath temperature from when the patient is healthy (i.e., when the breath temperature of the patient is 35° C.). Processing device 310 is configured to detect the onset of the exacerbation, when the relative percentage change of the breath temperature is greater than the relative percentage of the core body temperature. In one embodiment, the relative percentage change of the breath temperature is calculated by a) determining a difference between a current value of the breath temperature and the temperature of 35° C.; b) dividing this difference by the temperature of 35° C.; c) multiplying the result (i.e., obtained by dividing the difference by 35° C.) by 100 to obtain the relative percentage of the breath temperature. The current value of the core body temperature is obtained from core body temperature sensor 304.

If the determined relationship, or change in relationship, satisfies a predetermined criteria, then the method 100 proceeds to procedure 122. Otherwise, method 100 proceeds to procedure 104 where the core body temperature of the patient is monitored.

At procedure 122, an alarm indication or a warning may be generated by the alarm device 312 (as shown in and explained with respect to FIG. 3). The alarm indication may be generated to indicate that the onset of the exacerbations is detected. The alarm indication generated at procedure 122 may be then transmitted to a patient and/or a healthcare provider. The alarm indication generated may alert the patient to take appropriate action, for example, take medication or intervention steps. In one embodiment, intervention steps may include pulmonary rehabilitation. Method 100 ends at procedure 124.

Method 100 described above allows the detection of an early exacerbation via temperature monitoring. The calculated temperature change or relationship between the core body temperature and the exhaled breath temperature may also provide further information related to inflammation of the lungs.

Figure 2:
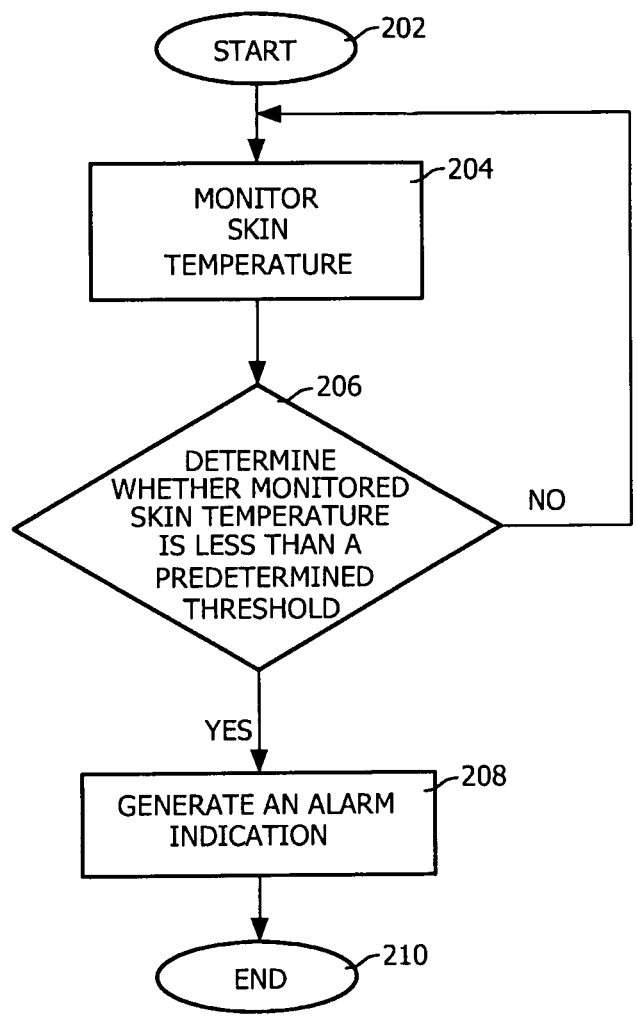
FIG. 2 illustrates a flow chart for a method for predicting an onset of cold stresses in the patient in accordance with an embodiment of the present invention.

FIG. 2 illustrates a flow chart for a method for predicting an onset of an exacerbation in the patient in accordance with another embodiment of the present invention. Method 200 is configured to detect an onset of cold stresses on the body of the patient using skin temperature of the patient. The cold stresses detected in the patient are generally linked to increased exacerbations.

If a cold stress on the body is detected in a patient (i.e., due to a predetermined decrease in the skin temperature), an indication or signal is generated to alert the patient to increase personal protection, e.g. extra clothing, heating, etc. Therefore, method 200 described below allows the prevention of cold stresses to the body and hence the aversion of an exacerbation.

Method 200 begins at procedure 202. At procedure 204, the skin temperature of the patient is monitored. This is done using a temperature sensor, such as sensor 306 (as shown in and explained with respect to FIG. 3). At procedure 206, the processor 310 (as shown in and explained with respect to FIG. 3) is configured to determine whether the monitored skin temperature is less than a predetermined threshold or exceeds a predetermined drop. In one embodiment, the predetermined threshold may include a temperature of 33° C. In another embodiment, the temperature drop is greater than 1° C. In one embodiment, the temperature drop may be a sudden drop or a gradual drop and may remain for a predetermined amount of time.

When the monitored skin temperature is less than the predetermined threshold, or drops more than the predetermined threshold, then method 200 proceeds to procedure 208. Otherwise, the method returns to procedure 204 where the skin temperature of the patient is monitored. At procedure 208, an alarm indication or a warning may be generated by alarm device 312 (as shown in and explained with respect to FIG. 3). The alarm indication may be generated to alert the patient to use increased personal protection (e.g., extra clothing and/or heating). Method 200 ends at procedure 210.

Because method 200 detects the cold stresses in the patient that are generally linked to increased exacerbations, in one embodiment, the method may be combined with method 100 to provide an additional indicator for the onset of the exacerbations in the patient. For example, in one embodiment, processor 310 is configured to detect an onset of an exacerbation, when the core body temperature and the breath temperature increased by a same amount or a predetermined percentage amount, and the skin temperature stays the same, does not increase as much percentage wise, or drops (e.g., 1° C. or more). In other words, processor 310 is configured to detect an onset of an exacerbation, when the monitored skin temperature of the patient is less than a predetermined threshold, or a drop in the monitored skin temperature of the patient exceeds a predetermined temperature drop; and coupled with the core body temperature and/or the breath temperature a) increasing by a predetermined amount, b) remaining constant, or c) dropping by an amount less than the drop in skin temperature either on an absolute or percentage basis.

System 300 for predicting the onset of an exacerbation in a patient in accordance with another embodiment of the present invention is shown in FIG. 3. In one embodiment, the system 300 of the present invention may be used by patients in the home environment of the patient. In another embodiment, the system 300 of the present invention may be used by a caregiver or healthcare provider. System 300 may include core temperature sensor 302, breath temperature sensor 304, skin temperature sensor 306, a user interface 308, processor 310, and alarm device 312.

In one embodiment, core body temperature sensor 302 is used to monitor the body temperature of the patient. In one embodiment, core body temperature sensor 302 may be in the form of a patch that is attached to the patient's body. In one embodiment, for improved accuracy (e.g., for accuracy of 0.3° C. or better), core body temperature sensor 302 may generally be placed in the forehead region of the patient. In an alternative embodiment, the core body temperature sensor may generally be placed in chest/abdominal region of the patient.

In one embodiment, core body temperature sensor 302 may be configured to measure the inner body temperature using a non-invasive technique. An example of such a technique is the zero-heat flux method as described in U.S. Pat. No. 3,933,045, the contents of each of which are hereby incorporated herein by reference.

The present invention contemplates that the core body temperature sensor may be any sensor suitable for making such measurement. Examples of suitable sensors are disclosed in European patent application nos. 08156802.4, 09157392.3, and 09155065.7 in PCT patent application publication nos. WO 2008/110948, WO 2008/110949, WO 2008/110947, WO 2008/068665, and WO 2008/078271 and in U.S. Patent Application Ser. Nos. 61/032,084 and 61/145,605, the contents of each of which are hereby incorporated herein by reference.

In one embodiment, an exhaled breath temperature sensor 304 may be used to monitor the breath temperature of the patient. In one embodiment, the breath temperature sensor may be an external device. In one embodiment, breath temperature sensor 304 may be integrally attached to core body temperature 302. In one embodiment, breath temperature sensor 304 may include a sensitive temperature sensor, such as a thermistor, or thermofoil, that measures the temperature profile of the breath before, during, and after exhaling. In such an embodiment, the patient exhales into the breath temperature sensor 304 (e.g., a mouth-piece attached to the breath temperature sensor 304) to measure the breath temperature. It is contemplated that other types of temperature sensing elements (i.e., instead of a thermistor) may be used to monitor the breath temperature. In one embodiment, breath temperature sensor 304 may include a breath thermometer. Such a breath thermometer may be a X-halo breath thermometer available from Delmedica. In one embodiment, a skin temperature sensor may be a Philips skin temperature probe (e.g., part number 989803162641). In one embodiment, a skin temperature sensor may be a SmartSense-800 wireless skin temperature sensor available from Cadi Scientific.

Figure 4:
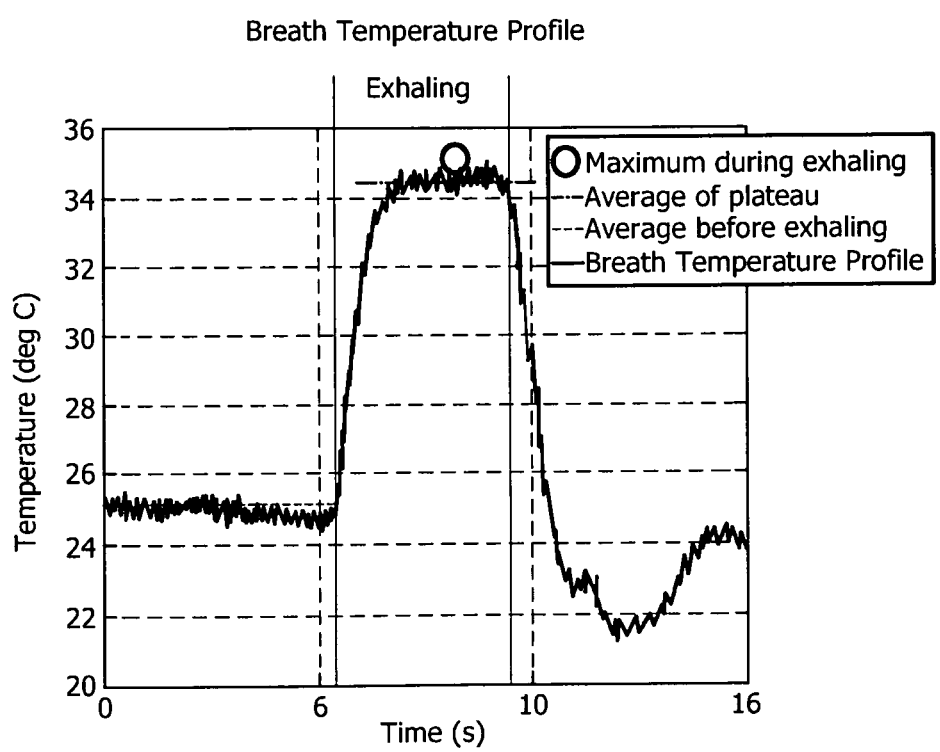
FIG. 4 is a graphical representation of an exemplary breath temperature profile of a health person.

FIG. 4 shows a graphical representation providing an exemplary breath temperature profile for a healthy patient. The graph illustrates the time, expressed in seconds, on a horizontal x-axis. On a vertical y-axis, the graph illustrates the temperature, expressed in centigrade. The ambient temperature as well as the breath temperature may be extracted from the breath temperature profile (shown in FIG. 4).

As shown in FIG. 4, the breath temperature of a healthy person is generally around 35° C., and the ambient temperature is generally around 25° C.

In one embodiment, from the temperature profile (as shown in FIG. 4), the maximum temperature value during exhalation phase is extracted as an indicator of the breath temperature. In an alternative embodiment, from the temperature profile (as shown in FIG. 4), an average temperature value during exhalation phase is extracted from the temperature profile as an indicator of the breath temperature.

In one embodiment, the breath temperature profile and derived parameters such as the average breath temperature value during exhalation, the slope of the breath temperature profile at the onset of exhalation, and/or the average breath temperature value before exhalation, may be obtained by continuously measuring with breath temperature sensor 304 and processing with processor 310.

An average breath temperature value before exhalation phase is extracted from the breath temperature profile as an indicator of the ambient temperature. The ambient temperature value may aid in the analysis of aversion of exacerbation and the prediction of cold stresses, together with the other collected temperature variables In one embodiment, the slope of the breath temperature profile at the onset of exhalation may also be used as an indicator for identifying exacerbations. In one embodiment, the breath temperature profile before exhalation phase may provide a reference for the calculation of the slope.

In one embodiment, a change in relationship in the breath temperature may be used in addition to using relationship, or a change in relationship, between core body temperature of the patient and (exhaled) breath temperature of the patient. In one embodiment, the change in relationship in the breath temperature may be a change in slope of the breath temperature.

Figure 5:
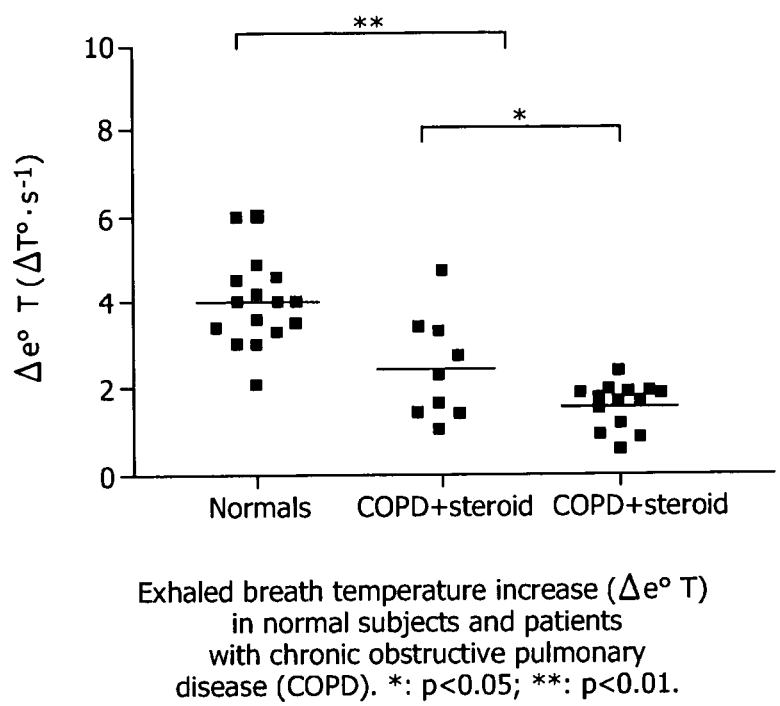
FIG. 5 is a graphical representation of an exemplary breath temperature increase in a healthy person, and a COPD patient with and without medication (e.g., steroids).

FIG. 5 is a graphical representation of an exemplary breath temperature increase or change in a healthy person, a COPD patient with medication (e.g., steroids) and a COPD patient without medication (e.g., steroids). The graph illustrates the exhaled breath temperature increase or change (e°T), expressed in $\Delta °T \cdot s^{-1}$, on a vertical y-axis. As can be seen in FIG. 5, COPD patients have a slower rate of temperature increase than a healthy person. The graphical representation also illustrates that introducing medication (which decreases inflammation) results in a faster rate of breath temperature increase. Therefore, the greater the inflammation, the slower the rate of breath temperature increase. In one embodiment, a decrease in the rate of breath temperature that is larger than (e.g., 10-15% from) the baseline rate of breath temperature increase may indicate an exacerbation in the COPD patient. In one embodiment, the exhaled breath temperature increase or change (i.e., slope) alone may be used to detect the exacerbation in the COPD patient without the core body temperature.

In one embodiment, rate of change of the breath temperature of the patient is further factored in detecting the onset of the exacerbations in the COPD patient.

In one embodiment, processor 310 may include a data storage unit or memory (not shown) that is constructed and arranged to store the core temperature, the skin temperature and the breath temperature of the patient. The stored data may be used for further processing, for example, for trending, and/or display.

In one embodiment, user interface 308 is in communication with processor 310. The user interface is configured to accept input from the patient, and to transmit (and display) output of system 300. In one embodiment, user interface 308 may include a keypad that allows the patient to input information (e.g., patient's core body temperature, patient's breath temperature, and/or patient's skin temperature) into processor 310. In one embodiment, the user interface may include a display screen that provides a visual data output (e.g., signal or alarm indication) to the patient. In one embodiment, the user interface 308 may include a speaker that provides an audio signal or alarm indication to the patient.

In one embodiment, user interface 308 may be a graphical user interface. In one embodiment, the user interface may be provided integral with the sensor set (i.e., the core body temperature sensor, the skin temperature sensor or the breath temperature sensor). In another embodiment, the user interface may be provided remote from or proximal to the sensor set.

Alarm device 312 may include a sound producing device and/or a visual indicator. The sound producing device, if provided, is constructed and arranged to generate an audio signal or alarm indication in response to the detection of the onset of the exacerbations in the patient. The visual indicator, if provided, is constructed and arranged to generate a visual signal or alarm indication in response to the detection of the onset of the exacerbations in the patient.

In one embodiment, the display screen of user interface 308 may function as a visual indicator. In one embodiment, the speaker integrally attached to the user interface may function as the sound producing device. In one embodiment, the sound producing device may include a speaker. In one embodiment, the audio signal or alarm indication may include, but not limited, to a tone, a buzz, a beep, a sound (e.g., a horn or a chime), and/or a prerecorded voice message. In one embodiment, the audio signal or alarm indication may include tones with changing frequency or volume. In one embodiment, the audio signal or alarm indication may include customer configurable tones and alarms.

In one embodiment, the visual indicator may include one or more lights, lamps, light emitting diodes and/or liquid crystal displays. In an embodiment, the visual signal or alarm indication may be generated by, for example, continuous, or flashing lights.

In one embodiment, alarm device 312 may also be configured to generate the signal or alarm indication a) when the core body temperature satisfies the first predetermined criteria, b) when the breath temperature of the patient satisfies the second predetermined criteria, c) when the skin temperature of the patient satisfies the third predetermined threshold, and/or d) when a predetermined relationship or change in relationship is met when comparing two or all three of the core body temperature, the breath temperature, and/or the skin temperature. In such embodiment, the alarm device 312 is configured to generate different signals or alarm indications (audio and/or visual) for each of the above described conditions.

In one embodiment, alarm device 312 may be a part of the core temperature sensor, the breath temperature sensor, or the skin temperature sensor. In one embodiment, the alarm device may be positioned, for example, on the patient to provide the signal or alarm indication to the patient. In another embodiment, alarm device 312 may be, for example, a stand alone device in the home environment of the patient to provide the signal or alarm indication to the patient. In such an embodiment, the alarm device may be connected to processor 310 over the network. Also, in such an embodiment, the alarm device may be configured to transmit the signal or alarm indication to a personal handheld device of the patient such as cellular phone, PDA, or other personal electronic device over a wired or a wireless network.

The alarm indication generated may alert the patient to take appropriate action, for example, take medication or intervention steps (e.g., smoking cessation). In one embodiment, it is also contemplated that system 300 may also be configured to transmit the signal or alarm indication to the healthcare provider over the network (wired or wireless, for example) so that the healthcare provider, for example, may prescribe an appropriate medication or action that needs to be taken by the patient.

In one embodiment, the skin temperature is measured using skin temperature sensor 306. In one embodiment, the skin temperature sensor is a thermistor that is used to measure the peripheral body temperature. It is contemplated that other types of temperature sensing elements (i.e., instead of a thermistor) may be used to monitor the skin temperature. In one embodiment, the skin temperature sensor 306 may be in the form of a patch that is attached to the body of the patient.

In one embodiment, the skin temperature sensor 306 may be integrally attached to core body temperature sensor 302. As described above, the core body temperature sensor may be configured to measure the inner body temperature using the non-invasive technique. Such non-invasive technique is performed using the heater to warm the patient's skin until the core body temperature is attained. The skin temperature need not be measured while this heater is active. The core body temperature can be measured intermittently during a day, and the skin temperature sensor may be used to measure the skin temperature during the periods when this heater is inactive. By doing so, both the core body temperature and skin temperature may be obtained throughout the day.

In an alternative embodiment, the core body temperature sensor is adapted to simultaneously measure core body temperature and skin temperature, enabling continuous measurement of both skin and core temperatures. In this embodiment, the core body temperature sensor consists of two parts, one part functioning like a zero-heat-flux sensor, and a second part containing a thermistor placed near the skin, but outside the region of influence of the heater of the first part. It is contemplated that other types of temperature sensing elements (i.e., instead of a thermistor) may be used to monitor the skin temperature.

In another embodiment, a core body temperature sensor as described in U.S. Pat. No. 7,299,090, the contents of which are hereby incorporated by reference, is used. Such a core body temperature sensor includes of a thermistor $T_1$ near the skin, a layer of thermal insulation, and a thermistor $T_2$ on the opposite side. Such a core body temperature sensor does not include a heater. The core body temperature is derived via the formula $T_c = T_1 + (K_s/K_b)*(T_1 - T_2)$, where $K_s$ and $K_b$ are the thermal conductivity of the sensor and human tissue respectively. In such an embodiment the skin temperature may be derived from $T_1$ value, therefore preventing the need of an additional skin temperature sensor.

In one embodiment, the core body temperature sensor may include a one-axis, a two-axis, or three-axis accelerometer, to measure breathing or respiration rate of the patient. The breathing or respiration rate may also be used as an additional indicator for predicting the onset of exacerbations. In such an embodiment, the sensor may be placed on the thorax of the patient.

In one embodiment, the core body temperature sensor may include a microphone, to measure breathing or respiration rate of the patient. The breathing sounds and breathing rate may also be used as an additional indicator for predicting the onset of exacerbations. In such an embodiment, the sensor may be placed in the neck area of the patient.

In one embodiment, the acquired measurements (i.e., any combination of the core temperature of the patient, and the breath temperature of the patient; and/or the skin temperature of the patient) may be used to calculate a single value, for example, an exacerbation risk score. The exacerbation risk score may be used in Early Warning Scoring Systems, for example, used by Rapid Response Teams. The exacerbation risk score may be used in the Early Warning Scoring Systems along with other known risk factors for deterioration, such as breathing rate, pulse rate, for example.

In one embodiment, it is contemplated that user interface 308, processor 310, and alarm device 312 may be integrated into sensors (i.e., the core temperature sensor 302, the breath temperature sensor 304 or the skin temperature sensor 306).

Embodiments of the invention, such as the processor, for example, may be made in hardware, firmware, software, or various combinations thereof. The invention may also be implemented as instructions stored on a machine-readable medium, which may be read and executed using one or more processors. In one embodiment, the machine-readable medium may include various mechanisms for storing and/or transmitting information in a form that can be read by a machine (e.g., a computing device). For example, a machine-readable storage medium may include read only memory, random access memory, magnetic disk storage media, optical storage media, flash memory devices, and other media for storing information, and a machine-readable transmission media may include forms of propagated signals, including carrier waves, infrared signals, digital signals, and other media for transmitting information. While firmware, software, routines, or instructions may be described in the above disclosure in terms of specific exemplary aspects and embodiments performing certain actions, it will be apparent that such descriptions are merely for the sake of convenience and that such actions in fact result from computing devices, processing devices, processors, controllers, or other devices or machines executing the firmware, software, routines, or instructions.

Although the invention has been described in detail for the purpose of illustration, it is to be understood that such detail is solely for that purpose and that the invention is not limited to the disclosed embodiments, but, on the contrary, is intended to cover modifications and equivalent arrangements that are within the spirit and scope of the appended claims. In addition, it is to be understood that the present invention contemplates that, to the extent possible, one or more features of any embodiment can be combined with one or more features of any other embodiment.

What is claimed is:

1. A system for predicting an onset of an exacerbation in a patient, the system comprising:
   a temperature sensor (i) placed on a patient's body and (ii) configured to continuously monitor a core body temperature of the patient during at least a time period;
   a breath temperature sensor (i) outside of the patient's mouth and not attached directly to the patient's body and (ii) configured to continuously monitor breath temperature of the patient during at least the time period; and
   one or more processors configured to:
      calculate, from the continuously monitored core body temperature and the continuously monitored breath temperature, a relationship, or a change in relationship, between the core body temperature and the breath temperature of the patient; and
      detect an onset of the exacerbation responsive to a calculated relationship, or a change in relationship, between the core body temperature and the breath temperature of the patient during the time period satisfying a predetermined criteria, and
      wherein detecting the onset of the exacerbation comprises detecting the onset of the exacerbation responsive to a relative percentage change of the breath temperature during the time period being greater than a relative percentage change of the core body temperature during the time period.

2. The system according to claim 1, wherein the predetermined criteria comprises a predetermined relative increase in the breath temperature relative to the core body temperature.

3. The system according to claim 1, wherein the predetermined criteria comprises an absolute temperature difference between the core body temperature and the breath temperature.

4. The system according to claim 1, wherein the one or more processors are configured to:
   determine whether the core body temperature becomes greater than a temperature threshold, wherein detecting the onset of the exacerbation comprises detecting the onset of the exacerbation further responsive to the core body temperature becoming greater than the temperature threshold.

5. The system according to claim 1, wherein the one or more processors are configured to:
determine whether the breath temperature becomes greater than a temperature threshold,
wherein detecting the onset of the exacerbation comprises detecting the onset of the exacerbation further responsive to the breath temperature becoming greater than the temperature threshold.

6. The system according to claim 1, further comprising:
a skin temperature sensor (i) placed on the patient's body and (ii) configured to continuously monitor skin temperature of the patient,
wherein the one or more processors are configured to determine whether the skin temperature falls below a temperature threshold, and
wherein detecting the onset of the exacerbation comprises detecting the onset of the exacerbation further responsive to the skin temperature of the patient falling below the temperature threshold.

7. The system according to claim 1, wherein the one or more processors are configured to:=
determine, from the continuously monitored core body temperature, a first core body temperature measurement and a current core body temperature measurement during the time period;
determine, from the continuously monitored exhaled breath temperature, a first breath temperature measurement and a current breath temperature measurement during the time period; and
determine, during the time period, (i) the relative percentage change of the core body temperature from the first core body temperature measurement and the current core body temperature measurement and (ii) the relative percentage change of the breath temperature from the first breath temperature measurement and the current breath temperature measurement.

8. A system for predicting an onset of an exacerbation in a patient, the system comprising:
a first sensor (i) placed on a patient's body and (ii) configured to continuously monitor a core body temperature of the patient during at least a time period;
a second sensor (i) outside of the patient's mouth and separated from the patient's body by at least a mouth piece and (ii) configured to continuously monitor breath temperature of the patient during at least the time period; and
one or more processors configured to:
determine, from the continuously monitored core body temperature, a relative percentage change of the breath temperature during the time period;
determine, from the continuously monitored breath temperature, a relative percentage change of the core body temperature during the time period; and
detect the onset of the exacerbation responsive to the relative percentage change of the breath temperature being greater than the relative percentage change of the core body temperature.

9. The system according to claim 8, wherein the one or more processors are configured to:
determine, from the continuously monitored core body temperature, a first core body temperature measurement and a current core body temperature measurement during the time period;
determine, from the continuously monitored exhaled breath temperature, a first breath temperature measurement and a current breath temperature measurement during the time period; and
wherein determining the relative percentage change of the core body temperature comprises determining the relative percentage change of the core body temperature from the first core body temperature measurement and the current core body temperature measurement, and
wherein determining the relative percentage change of the breath temperature comprises determining the relative percentage change of the breath temperature from the first breath temperature measurement and the current breath temperature measurement.

10. The system according to claim 8, wherein detecting the onset of the exacerbation comprises detecting the onset of the exacerbation further responsive to the core body temperature becoming greater than a temperature threshold.

11. The system according to claim 8, wherein detecting the onset of the exacerbation comprises detecting the onset of the exacerbation further responsive to the breath temperature becoming greater than the temperature threshold.

12. The system according to claim 8, further comprising:
a third sensor (i) placed on the patient's body and (ii) configured to continuously monitor skin temperature of the patient, wherein detecting the onset of the exacerbation comprises detecting the onset of the exacerbation further responsive to the skin temperature of the patient falling below a temperature threshold.

13. A method for predicting an onset of an exacerbation in a patient, the method comprising:
continuously monitoring, via a first sensor placed on a patient's body, a core body temperature of the patient during at least a time period;
continuously monitoring, via a second sensor outside of the patient's mouth and separated from the patient's body by at least a mouth piece, a breath temperature of the patient during at least the time period;
determining, from the continuously monitored core body temperature, a relative percentage change of the breath temperature during the time period;
determining, from the continuously monitored breath temperature, a relative percentage change of the core body temperature during the time period; and
detecting the onset of the exacerbation responsive to the relative percentage change of the breath temperature being greater than the relative percentage change of the core body temperature.

14. The method according to claim 13, further comprising:
determining, from the continuously monitored core body temperature, a first core body temperature measurement and a current core body temperature measurement during the time period;
determining, from the continuously monitored exhaled breath temperature, a first breath temperature measurement and a current breath temperature measurement during the time period; and
wherein determining the relative percentage change of the core body temperature comprises determining the relative percentage change of the core body temperature from the first core body temperature measurement and the current core body temperature measurement, and
wherein determining the relative percentage change of the breath temperature comprises determining the relative percentage change of the breath temperature from the first breath temperature measurement and the current breath temperature measurement.

15. The method according to claim 13, wherein detecting the onset of the exacerbation comprises detecting the onset of the exacerbation further responsive to the core body temperature becoming greater than a temperature threshold.

16. The method according to claim 13, wherein detecting the onset of the exacerbation comprises detecting the onset of the exacerbation further responsive to the breath temperature becoming greater than the temperature threshold.

17. The method according to claim 13, further comprising:
 continuously monitoring, via a third sensor placed on the patient's body, a skin temperature of the patient during at least the time period, wherein detecting the onset of the exacerbation comprises detecting the onset of the exacerbation further responsive to the skin temperature of the patient falling below a temperature threshold.

* * * * *